United States Patent [19]

Levinthal

[11] Patent Number: 4,925,936
[45] Date of Patent: May 15, 1990

[54] RECOVERY OF NITRIC ACID AND SULFURIC ACIDS IN PRODUCTION OF BETA HMX

[75] Inventor: Michael L. Levinthal, Marshall, Tex.

[73] Assignee: Thiokol Corporation, Chicago, Ill.

[21] Appl. No.: 365,105

[22] Filed: Jun. 12, 1989

[51] Int. Cl.$^5$ .................................. C07D 225/02
[52] U.S. Cl. ............................................. 540/475
[58] Field of Search ................................ 540/475

[56] References Cited

U.S. PATENT DOCUMENTS 4,163,845  8/1979  Brumley ........................... 540/475
4,785,094  11/1988  Levinthal ......................... 540/475

OTHER PUBLICATIONS

Gericke, D., Concentration of Nitric Acid by Sulphuric Acid, Chemie-Ingenieur-Technik 21/74, pp. 894–899.
Rodger, I., Developments in the Concentration of Sulfuric Acid, AICHE Journal 1982.
Sloan, J. G., "The Extractive Distillation Process for Nitric Acid Concentration Using Magnesium Nitrate".

Primary Examiner—David B. Springer
Attorney, Agent, or Firm—Parmelee, Bollinger & Bramblett

[57] ABSTRACT

Recovery of sulfuric and nitric acids from spent acid streams in a process for producing beta HMX in which hexamine, ammonia and acetic anhydride are reacted to produce DAPT, the DAPT is treated with a mixture of sulfuric and nitric acids to produce DADN which is then nitrolyzed with $N_2O_5$ and anhydrous nitric acid to produce a HMX solution which is added to a dispersion of beta HMX seed crystals in water to selectively precipitate beta HMX from the HMX solution is accomplished by maintaining the DAPT/DADN spent acid stream separate from the HMX spent acid stream and treating the DAPT/DADN spent acid stream in a sulfuric acid recovery unit and treating the HMX spent acid stream in a magnesium nitrate nitric acid recovery unit.

11 Claims, 3 Drawing Sheets

RECOVERY OF NITRIC ACID AND SULFURIC ACIDS IN PRODUCTION OF BETA HMX

The U.S. Government has rights in this invention pursuant to Contract No. DAAA09-87-Z-0014 awarded by the U.S. Army.

FIELD OF THE INVENTION

The present invention relates to a process for the recovery of sulfuric and nitric acid employed during a process employed to produce crystalline HMX in the beta form.

BACKGROUND OF THE INVENTION

HMX is a crystalline solid used as an explosive and as an ingredient of propellants, primarily in military applications. HMX is crystalline octahydro-1,3,5,7-tetranitro-1,3,5,7-tetrazine, alternatively known as cyclotetramethylenetetranitramine; 1,3,5,7-tetranitro-1,3,5,7-tetraazacyclooctane; homocyclonite; octagen; or by Chemical Abstracts Registry No. 2691-41-0. It is polymorphic, having four crystalline forms commonly known as alpha HMX, beta HMX, gamma HMX, and delta HMX. Beta HMX is considered to be the least impact sensitive of the four, and for that reason is the only form of HMX which meets present military specifications. For reasons of safety and efficiency, it is desirable to crystallize HMX in the beta form exclusively.

Recently, a process has been disclosed to obtain HMX in the beta form substantially exclusively, namely in U.S. Pat. No. 4,785,094 of the present Applicant, which issued Nov. 15, 1988 and is assigned to Morton Thiokol, Inc. In said process an unsaturated solution of HMX in a solvent consisting essentially of nitric acid is added to a dispersion of beta HMX seed crystals in water to precipitate beta HMX selectively from the solution of HMX.

This aforementioned precipitation step for the production of beta HMX crystals is the last stage of a process beginning with the reaction of hexamine and acetic anhydride. The reaction sequence for the production of the unsaturated HMX solution to add to the dispersion of beta HMX crystals in water is as follows:

(a) production of diacetyl pentamethylenetetraamine (DAPT):

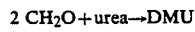

(b) reforming hexamine by using ammonia to react with the formaldehyde generated in the DAPT production:

$$6\ CH_2O + 4\ NH_3 \rightarrow hexamine + 6\ H_2O$$

(c) production of 1,5-diacetyl-3,7-dinitro-1,3,5,7-tetraazacyclooctane (DADN):

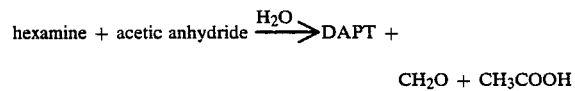

$$DADN + CH_2O + H_2O$$

with the formaldehyde generated reacting with urea to form dimethylol urea (DMU)

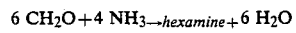

to prevent the formaldehyde from reacting with nitric acid (d) production of unsaturated HMX solution:

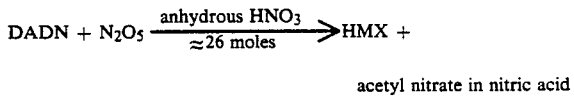

acetyl nitrate in nitric acid

An important economic consideration in this improved process for the production of beta HMX resides in the ability to recover the sulfuric and nitric from the process steps. In the recovery of acid from the process, an important consideration would be the ability to destroy or isolate any organics (mostly DMU, HMX and DADN fines) in the spent acid stream.

Owing to the physical behavior of water/nitric acid systems, it is not possible by a standard distillation or rectification process to remove excessive water from the acid since the mixture forms an azeotrope with a maximum boiling point at about 69% wt $HNO_3$ at 120.5° C. Thus, it has been known for a long time that by adding sulfuric acid to a nitric acid/water mixture the boiling behavior of the latter can be altered so that concentrated nitric acid can be distilled off and concentrated sulfuric acid recovered in a sulfuric acid concentrator. Such a process is reviewed, for example, in Gericke, D.; Concentration of Nitric Acid by Sulphuric Acid, Chemie-Ingenieur-Technik 21/74 pp. 894–899.

Thus, it appeared that an easy and convenient solution to the recovery of acids in the hereinbefore mentioned improved process for the production of beta HMX would reside in mixing the spent acid stream so that strong sulfuric acid could break the nitric acid/water azeotrope to permit stripping of substantially all the nitric acid out of the mixture at a level of about 98% minimum concentrated nitric acid. Thereafter, the remaining sulfuric acid and water mixture could be sent to a sulfuric acid concentrator to boil off the water and recover about 93% minimum concentrated sulfuric acid. It was also to be assumed that the combination of hot sulfuric and nitric acid would lead to the destruction of any organics, such as DMU, DADN and/or HMX in the spent acid stream. However, it was discovered that such an apparent solution to the recovery of spent acids in the improved beta HMX production process presented various undesirable drawbacks, such as for example, high capital and operating costs, the non-destruction of DMU in the hot, spent mixed acid stream, the non-flexibility of the feed stream concentrations and the mixing or integration of the nonexplosive portion of the process (DAPT/DADN production) with the potentially explosive portion of the process (HMX production and recrystallization).

Thus, a need arose for an acid recovery system for the beta HMX production process that would avoid most of all of these drawbacks and which would be economical and efficient to operate.

BRIEF DESCRIPTION OF THE DRAWINGS

The invention will be explained in reference to the accompanying drawings in which.

SUMMARY OF THE INVENTION

Figure 1:
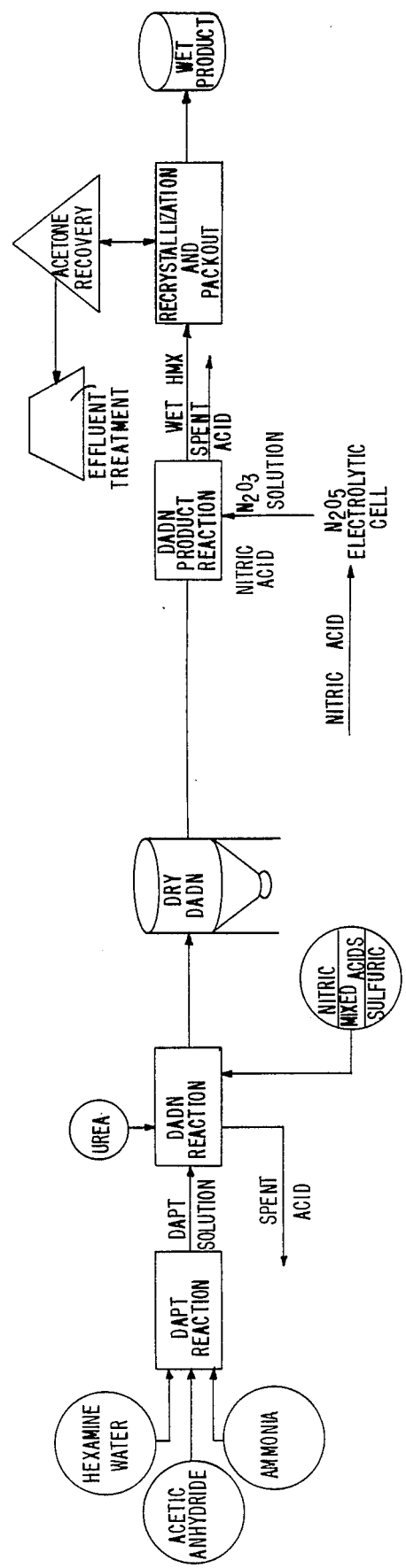
FIG. 1 is an overall schematic of the process for the production of beta HMX.

It has been discovered that an effective and efficient process for the recovery of spent acids from the improved process for the production of beta HMX, as described in the BACKGROUND OF THE INVENTION and illustrated schematically in FIG. 1, could be obtained if the DAPT/DADN spent acid was separated from the electrolytic cell/HMX spent acid. In this manner, a sulfuric acid recovery unit (SAC unit) could be employed to concentrate sulfuric acid to about 93% from the DAPT/DADN spent stream which contains sulfuric acid and water with a small amount of nitric and acetic acids and possibly some organics, such as DMU and/or DADN, and a magnesium nitrate unit (Maggie unit) nitric acid concentrator could be employed to break the nitric acid/water azeotrope in the electrolytic cell/HMX spent acid stream which contains nitric acid, a small amount of acetic acid and water with no sulfuric acid being present.

DETAILED DESCRIPTION OF THE INVENTION

In the process for producing beta HMX according to this invention when DAPT and DADN are produced as described hereinbefore and as illustrated schematically in FIG. 1, the DAPT/DADN spent acid stream was found to contain mostly sulfuric acid with a small amount of nitric and acetic acids and possibly a small amount of organics such as DMU or DADN fines. A typical spent acid stream from the DAPT/DADN process steps has been found to comprise about 30% sulfuric acid, 2.3% acetic acid, 3.0% nitric acid, about 63.4% water and up to about 1.3% organics such as DMU or DADN fines. It has been discovered that such a spent acid stream can be treated in a multistage sulfuric acid concentrator unit to concentrate and recover sulfuric acid to 93% or more. The water, acetic acid and nitric acid coming overhead from the concentrator unit is mostly water, about 91%, and could be treated by neutralization as an effluent. The tests conducted in such a unit demonstrate that most organics not going overhead would be destroyed by the 160°–170° C. sulfuric acid.

The suitability and effectiveness of a sulfuric acid concentrator (one stage, vacuum) in treating the DAPT/DADN spent acid stream is demonstrated in the following Examples 1 to 3. In these examples a one stage sulfuric acid vacuum concentrator batch unit in laboratory glassware using an uninsulated, ice-water cooled Liebig condenser, and a graduated glass receiver was employed. Heat input was from an electric mantle on the 500 ml flask (the still pot). The pot was heated, ultimately to 165° C. with 50 mm Hg vacuum (absolute) applied through a lab vacuum system. The pot was charged with a DAPT/DADN simulated spent acid stream as set forth in the examples. Results of those distillations are shown in Table I.

TABLE I

| SULFURIC ACID CONCENTRATOR DISTILLATION DATA | | | | | | |
|---|---|---|---|---|---|---|
| EXAMPLE 1 | | | | | | |
| Stream: 2.5% $CH_3COOH$, 3.0% $HNO_3$, 30% $H_2SO_4$, 1% DADN, 63.5% $H_2O$ | | | | | | |
| Sample | Boiling Range (°C.) | Weight (grams) | Titrated Acid (%) | % HOAc | % $HNO_3$ | % $H_2SO_4$ |
| | | | | Ion Chromatography | | |
| Original | — | 345 | — | 3.0 | 2.4 | 29.4 |
| 1 | 21–67 | 62.3 | 5.2 | 3.6 | 0 | 0 |
| 2 | 75–107 | 113.5 | 11.0 | 2.5 | 3.5 | 0 |
| 3 | 107–173 | 38.5 | 5.4 | 0 | 3.8 | 0.7 |
| 4 | — | 120.6 | 85.3 | 0 | 0 | 73.4 |
| EXAMPLE 2 | | | | | | |
| Stream: 2.5% $CH_3COOH$, 3.0% $HNO_3$, 30% $H_2SO_4$, 64.5% $H_2O$ | | | | | | |
| Fraction | Boiling Range (°C.) | Weight (grams) | Titrated Acid (%) | % HOAc | % $HNO_3$ | % $H_2SO_4$ |
| | | | | Ion Chromatography | | |
| Original | — | 336 | — | 1.9 | 3.3 | 31.3 |
| 1 | 21–66 | 52.7 | 4.5 | 0.3 | 0 | 0 |
| 2 | 67–95 | 107.1 | 11.2 | 0.3 | 4.0 | 0 |
| 3 | 95–166 | 36.5 | 10.2 | 0 | 2.9 | 0 |
| Pot | — | 125.6 | 84.2 | 0 | 0 | 100.0 |
| EXAMPLE 3 | | | | | | |
| Stream: 2.5% $CH_3COOH$, 3.0% $HNO_3$, 30% $H_2SO_4$, 64.5% $H_2O$ | | | | | | |
| Fraction | Boiling Range (°C.) | Weight (grams) | Titrated Acid (%) | % HOAc | % $HNO_3$ | % $H_2SO_4$ |
| | | | | Ion Chromatography | | |
| Original | — | 336 | — | 1.9 | 3.3 | 31.3 |
| 1 | 20–66 | 57.0 | 4.0 | 2.5 | 0 | 0 |
| 2 | 68–104 | 103.7 | 7.6 | 2.8 | 3.9 | 0 |
| 3 | 104–166 | 36.0 | 13.4 | <0.1 | 1.64 | 0 |
| Pot | — | 128.4 | 84.6 | 0 | 0 | 100.0 |
| EXAMPLE 4 | | | | | | |
| Stream: 2.5% $CH_3COOH$, 3.0% $HNO_3$, 30% $H_2SO_4$, 1% DMU, 63.5% $H_2O$ | | | | | | |
| Fraction | Boiling Range (°C.) | Weight (grams) | DMU Content (grams) | Titrated Acid (%) | % HOAc | % $HNO_3$ | %$H_2SO_4$ |
| | | | | | Ion Chromatography | | |
| Original | — | 346 | 3.4 | — | 2.5 | 3.5 | 30 |
| 1 | 25–71 | 79 | 1.8 | 4.4 | 4.8 | 0 | 0 |
| 2 | 72–100 | 85 | 1.5 | 9.7 | 6.2 | 4.5 | 0 |

TABLE I-continued
SULFURIC ACID CONCENTRATOR DISTILLATION DATA

| 3 | 100–175 | 40 | 0 | 3.9 | 0.4 | 2.8 | 0 |
|---|---------|-----|------|-------|-----|-----|-------|
| Pot | — | 128 | 0 | 83.9 | 0.6 | 0.7 | 85.5 |
| % Recovery | — | 96.0 | 97.1 | 100.8 | 115 | 48 | 103 |

A few grams of DADN was added to the pot in Example 1. There as an exotherm when the pot reached 74° C. accompanied by a pressure excursion, indicating that the DADN decomposed. Subsequent HPLC analysis of the still bottoms and the collected distillate fractions confirmed the lack of DADN (method detection limit=1 ppm). The pot and collected distillate fractions were analyzed by titration for total acidity and ion chromatography for species identification.

A few grams of DMU was added to the simulated spent acid stream in Example 4. The DMU all goes overhead with none remaining in the sulfuric acid. Thus, there will be no buildup of DMU in the recovered sulfuric acid to be recycled to the HMX production process. The DMU would therefore be sent to neutralization along with the acetic and nitric acids from the sulfuric acid concentrator where the DMU may survive the neutralization step and be lost.

In all the examples sulfuric acid of at least 93% concentration is readily recovered from the spent acid streams.

When beta HMX is produced from DADN according to this invention as described hereinbefore, the electrolytic cell/HMX spent acid stream was found to typically contain about 52.8% nitric acid, about 44.7% water and about 2.5% acetic acid and possibly some minor amount of HMX. It has been discovered that such a spent acid stream can be treated in a multistage magnesium nitrate concentrator and thereby recover nitric acid of a concentration of 90% or more, generally 98%.

In another series of examples, the suitability and effectiveness of a magnesium nitrate concentrator ("Maggie" unit) in treating the electrolyte cell/HMX spent acid stream is demonstrated. In these examples a Maggie batch unit in laboratory glasswater similar to the sulfuric unit described above, an uninsulated 5 or 15 plate, Ace D6565 perforated plate column, with or without jacket as indicated, but without vacuum for the part of the distillation recovering the nitric acid, and full vacuum for reconstituting the magnesium nitrate was employed. The distillation of nitric acid used a 5.3/1 ratio of magnesium nitrate to acid solution. In each of said Examples 5 to 8 the simulated electrolyte cell/HMX spent acid stream comprised an acid solution consisting of 52.8% nitric acid, 44.7% water and 2.5% acetic acid. The magnesium nitrate concentration was 72% in water. Results of these distillation examples are shown in Table II.

TABLE II
MAGGIE DISTILLATION DATA

| Fractions | Boiling Range (°C.) | Weight (grams) | Titrated Acid (%) | % HOAc Ion Chromatography | % HNO₃ Ion Chromatography |
|---|---|---|---|---|---|
| EXAMPLE 5 | | | | | |
| Column: Ace D6565 perforated 5 plate without jacket | | | | | |
| Original | — | 52.3 | — | 2.5 | 53.0 |
| 1 | 81–83 | 20.9 | 98.2 | 0.0 | 99.2 |
| 2 | 83–92 | 1.2 | 100.0 | 0.1 | 90.2 |
| 3 | 50* | 17.1 | 36.0 | 5.9 | 34.2 |
| Recovery | — | 75.0% | — | 67.0 | 94.0 |
| EXAMPLE 6 | | | | | |
| Column: Ace D6565 perforated 15 plate with jacket | | | | | |
| Original | — | 57.9 | — | — | — |
| 1 | 81–85 | 17.1 | 100.0 | 0.0 | 96.9 |
| 2 | 114–117 | 21.8 | 38.3 | 4.4 | 35.2 |
| 3 | 31* | 17.7 | 29.3 | 1.6 | 25.2 |
| Recovery | — | 97.8% | — | 82.3 | 96.2 |
| EXAMPLE 7 | | | | | |
| Column: Ace D6565 perforated 15 plate with jacket | | | | | |
| Original | — | 57.0 | — | 1.1 | 60.0 |
| 1 | 81–84 | 16.8 | 100.7 | 0.0 | 92.7 |
| 2 | 116–117 | 11.0 | 40.9 | 3.0 | 34.1 |
| 3 | 48–50* | 19.7 | 33.2 | 2.6 | 36.2 |
| Recovery | — | 86.4% | — | 56.2 | 94.8 |
| EXAMPLE 8 | | | | | |
| Column: Ace D6565 perforated 15 plate with jacket | | | | | |
| Original | — | 56.1 | — | 3.0 | 58.6 |
| 1 | 80–82 | 19.9 | 100.0 | 0.0 | 93.7 |
| 2 | 115–117 | 17.6 | 43.9 | 5.3 | 38.9 |
| 3 | 50* | 19.3 | 13.9 | 2.0 | 14.2 |
| Recovery | — | 100.0% | — | 78.4 | 89.7 |
| Average Recovery | | 94.7 | — | 72.3 | 99.3 |

*Under vacuum

The distillation residue contained water and acetic acid with the magnesium nitrate. To reconstitute the magnesium nitrate, the flask was heated to 125° C. with application of full vacuum and the resultant slurry consisted of about 72% magnesium nitrate and 28% water. In said examples the distillates were analyzed for total acidity by titration and species were confirmed by ion chromatography.

Figure 2:
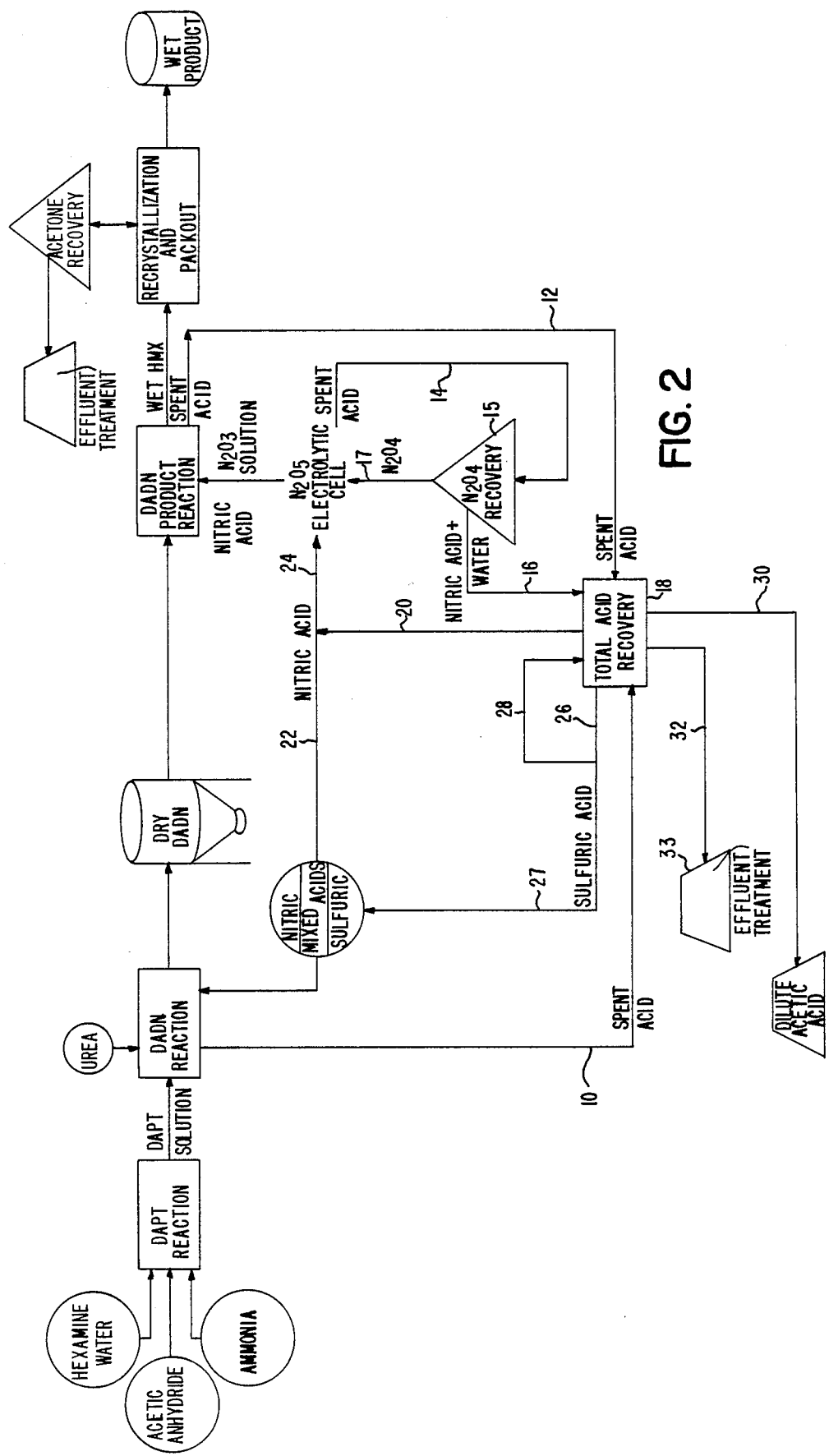
FIG. 2 is an overall schematic of the readily apparent available process for the recovery of spent acids from the process of FIG. 1 employing sulfuric acid to alter the behavior of a nitric acid-water mixture.

The drawings illustrate the usefulness and advantages of employing the recovery system of this invention with the improved beta HMX process as described in the Background Of The Invention. FIG. 1 schematically represents the improved beta HMX process described fully in said Background Of The Invention section. FIG. 2 schematically illustrates the undesirable process for the recovery of the spent acids streams from the hereintofore described process of FIG. 1 for producing beta HMX. In said process the spent acid streams from the various parts of the process would be combined so that the sulfuric acid in the mixed acid streams would be available to break the nitric acid-water azeotrope to enable recovery of both sulfuric and nitric acids. In such an acid recovery process, the spent acid streams from both the explosive portions of the HMX production process, i.e. the electrolytic cell/HMX portion, and the nonexplosive portion, i.e. the DAPT/DADN portion, are combined in a single acid recovery unit. Spent unit from the DAPT/DADN portion in line 10 as well as spent acid from both the beta HMX seed step in line 12 and spent acid from electrolyte cell in line 14 processed in N₂O₄ recovery unit 15 and discharged in line 16 is sent to a total acid recovery unit 18. Recovered N₂O₄ is fed by line 17 to the electrolyte cell. Concentrated nitric acid is recovered from said acid recovery unit 18 and fed by line 20 to either the electrolytic cell through line 24 or to the mixed acid holding vessel through line 22. Concentrated sulfuric acid is also recovered from said unit 18 and fed by line 26 to a mixed acid holding vessel by line 27 or recycled to the acid recovery unit 18 by line 28. Dilute acetic acid is recovered from the unit 18 by line 30 and effluent leaves unit 18 by line 32 to an effluent treatment unit 33. Such a total acid recovery process is burdened by the disadvantages discussed hereinbefore in the Background Of The Invention section.

Figure 3:
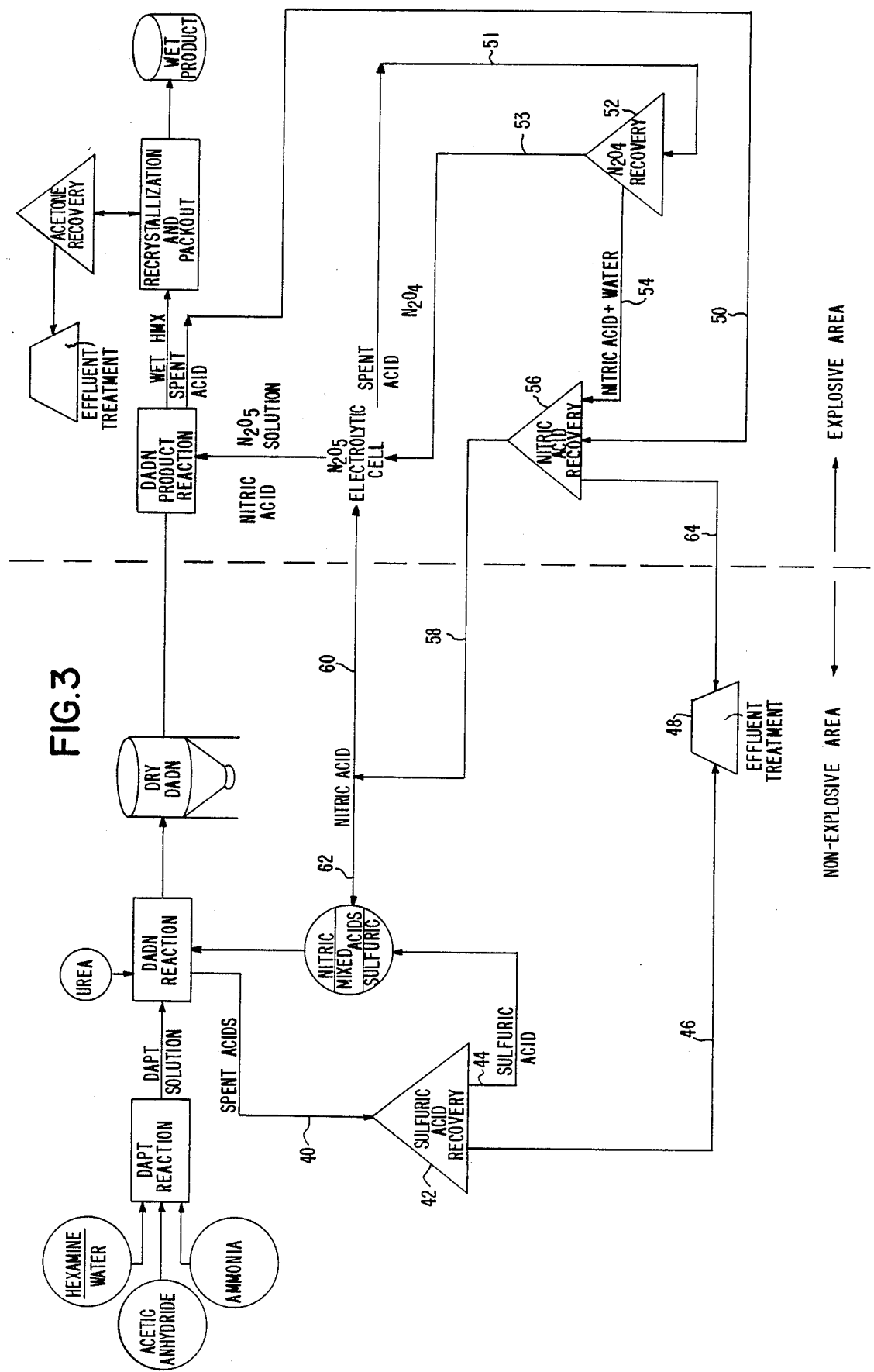
FIG. 3 is an overall schematic of the process for recovery of spent acids from the beta HMX production process according to the present invention.

Use of the acid recovery process of the present invention is illustrated schematically in FIG. 3. In reference to said Figure, it is readily seen that the spent acid streams for the explosive and nonexplosive units can be kept separate. In the recovery process according to the invention spent acid from the DAPT/DADN portion of the reaction sequence is fed by line 40 to a sulfuric acid recovery unit 42 where concentrated sulfuric acid is recovered and fed by line 44 to a mixed acids holding vessel. Effluent from unit 42 is fed by line 46 to an effluent treatment unit 48. Alternatively, this effluent could, if desired, be fed to the nitric acid recovery unit 56 to obtain additional nitric acid from this effluent. Spent acid from the beta HMX seed step is fed by line 50 to nitric acid recovery unit 56 as is the spent acid stream from the electrolytic cell by line 51 through $N_2O_4$ recovery unit 52 and then by line 54 to nitric acid recovery unit 56. Recovered $N_2O_4$ is fed by line 53 to the electrolytic cell. Concentrated nitric acid from unit 56 is fed by line 58 to the electrolytic cell by line 60 or to the mixed acid holding vessel by line 62. Effluent from the unit 56 is sent by line 64 to effluent recovery unit 48.

The use of the separate acid recovery units according to the present invention not only produces the desired concentrated sulfuric and nitric acids for reuse in the process in a manner that allows for separation of the nonexplosive and possibly explosive parts of the beta HMX production process but also has been proven to allow for lower capital and operating costs for such as acid recovery system.

Moreover, sulfuric acid concentrator units and magnesium nitrate nitric acid concentrator units are readily known and available for use in the improved acid recovery process of this invention. For example, to treat a DAPT/DADN spent acid feed stream 40 a suitable sulfuric acid recovery unit 42 to produce 8.5 tons/day of 93% sulfuric acid from such a feed stream containing about 31% sulfuric acid would be a three stage evaporator with operating conditions as follows:

|  | Outlet Acid Concentration | Temperature | Pressure |
| --- | --- | --- | --- |
| First Stage Boiler | 71 wt % | 165.5° C. | 760 mm Hg. |
| Second Stage Boiler | 88 wt % | 171° C. | 70 mm Hg. |
| Third Stage Boiler | 93 wt % | 176.6° C. | 20 mm Hg. |

The first, second and third stages boilers can be horizontal kettles made of glass-lined steel with a steam heated tantalum bayonet heater.

Similarly, to treat the electrolytic cell/HMX spent acid streams 50 and 54, a suitable nitric acid recovery unit 56 to produce 290 kg/hr concentrated (98%) nitric acid could consist of three main parts comprising a nitric acid preconcentrator, a nitric acid high concentrator and a magnesium nitrate reconcentrator. In the preconcentrator, water is evaporated concentrating the spent acid feed stream to about 67% nitric acid. In the high concentration unit, the preconcentrated nitric acid is admitted and treated with a concentrated, about 72%, magnesium nitrate solution, and concentrated to about 98% nitric acid. The bottom's liquid form the high concentrator, containing about 61% magnesium nitrate and less than about 0.1% nitric acid, is fed to the magnesium nitrate reconcentrator and reconcentrated to 72% magnesium nitrate which reconcentrated magnesium nitrate solution can be fed back to the nitric acid high concentrator.

It will be understood by those skilled in the art that the design of the particular sulfuric acid recovery unit and the particular magnesium nitrate nitric acid recovery unit will be dependent upon the capacity of the beta HMX production facility and other similar considerations and that the foregoing discussion of suitable units are merely exemplary for one illustrative beta HMX production line. All percentages in the specification are percent by weight unless indicated otherwise.

What is claimed is:

1. In a process for the production of beta HMX by reacting hexamine, ammonia and acetic anhydride to produce diacetyl pentamethylenetetraamine (DAPT) in acetic acid and adding said DAPT to a mixture of nitric and sulfuric acids to convert the DAPT to 1,5-diacetyl-3,7-dinitro-1,3,5,7-tetraazacylooctane (DADN), which DADN is nitrolyzed with nitrogen pentoxide and anhydrous nitric acid to form an HMX solution and the HMX solution is added to a dispersion of beta HMX seed crystals in water to precipitate beta HMX selectively from the HMX solution the improvement comprising recovering the spent sulfuric and nitric acid employed in said beta HMX production process by a process comprising maintaining the spent acid in the DAPT/DADN production steps separate from spent acid from the HMX production steps and treating the spent acid from the DAPT/DADN production steps in a sulfuric acid recovery unit to recover sulfuric acid of a concentration of at least 93% wt. and separately treating the spent acid from the HMX production steps in a magnesium nitrate nitric acid recovery unit to recover nitric acid of a concentration of at least about 90% wt.

2. A process according to claim 1 wherein the sulfuric acid recovery unit is a three stage evaporator in which the outlet sulfuric acid concentration in a first stage is about 71% wt., in a second stage is about 88% wt. and in a third stage is about 93% wt.

3. A process according to claim 1 wherein the magnesium nitrate nitric acid recovery unit comprises a nitric acid preconcentrator, a nitric acid high concentrator and a magnesium nitrate reconcentrator in which the outlet nitric acid from the nitric acid preconcentrator is about 67% wt. and from the nitric acid high concentrator is about 98% wt.

4. A process according to claim 2 wherein the magnesium nitrate nitric acid recovery unit comprises a nitric acid preconcentrator, a nitric acid high concentrator and a magnesium nitrate reconcentrator in which the outlet nitric acid from the nitric acid preconcentrator is about 67% wt. and from the nitric acid high concentrator is about 98% wt.

5. A process according to claim 1 wherein the nitrogen pentoxide reactant is produced in an electrolytic cell from $N_2O_4$ and nitric acid and spent acid from said electrolytic cell is fed to the magnesium nitrate nitric acid recovery unit for recovery of concentrated nitric acid.

6. A process according to claim 2 wherein the nitrogen pentoxide reactant is produced in an electrolytic cell from $N_2O_4$ and nitric acid and spent acid from said electrolytic cell is fed to the magnesium nitrate nitric acid recovery unit for recovery of concentrated nitric acid.

7. A process according to claim 3 wherein the nitrogen pentoxide reactant is produced in an electrolytic cell from $N_2O_4$ and nitric acid and spent acid from said electrolytic cell is fed to the magnesium nitrate nitric acid recovery unit for recovery of concentrated nitric acid.

8. A process according to claim 4 wherein the nitrogen pentoxide reactant is produced in an electrolytic cell from $N_2O_4$ and nitric acid and spent acid from said electrolytic cell is fed to the magnesium nitrate nitric acid recovery unit for recovery of concentrated nitric acid.

9. A process according to claim 1 wherein effluent from the su*lfuric acid recovery unit is fed to the magnesium nitrate nitric acid recovery unit for recovery of nitric acid in said effluent.

10. A process according to claim 4 wherein effluent from the sulfuric acid recovery unit is fed to the magnesium nitrate nitric acid recovery unit for recovery of nitric acid in said effluent.

11. A process according to claim 8 wherein effluent from the sulfuric acid recovery unit is fed to the magnesium nitrate nitric acid recovery unit for recovery of nitric acid in said effluent.

* * * * *